United States Patent [19] [11] 4,122,857
Haerr [45] Oct. 31, 1978

[54] PAD FOR ANCHORING AN ARTICLE TO THE SKIN OF A PATIENT

[75] Inventor: Raymond H. Haerr, Cincinnati, Ohio

[73] Assignee: Xomed Inc., Jacksonville, Fla.

[21] Appl. No.: 762,777

[22] Filed: Jan. 25, 1977

[51] Int. Cl.² .................................... A61M 25/02
[52] U.S. Cl. ................................. 128/348; 128/133; 128/DIG. 26; 248/205 A
[58] Field of Search .............................. 128/348–351, 128/133, DIG. 26; 248/205 A, 74 R; 24/16 R, DIG. 11; 174/117 A

[56] References Cited

U.S. PATENT DOCUMENTS

| 3,146,778 | 9/1964 | Krawiec | 128/349 R |
| 3,430,300 | 3/1969 | Doan | 24/73 |
| 3,826,254 | 7/1974 | Mellor | 128/133 |
| 3,834,380 | 9/1974 | Boyd | 128/133 |
| 3,918,446 | 11/1975 | Buttaravoli | 128/133 |

Primary Examiner—Dalton L. Truluck
Attorney, Agent, or Firm—J. Warren Kinney, Jr.

[57] ABSTRACT

A substantially rectangular pad of soft, strong, flexible, foam material is provided with a securement flap by which an article such as a catheter tube or the like may be anchored to the pad which in turn is adapted to be adhesively affixed to the skin of a patient.

14 Claims, 19 Drawing Figures

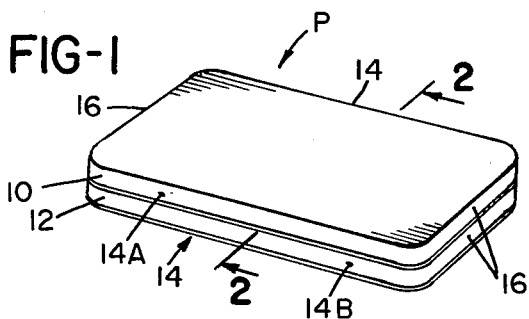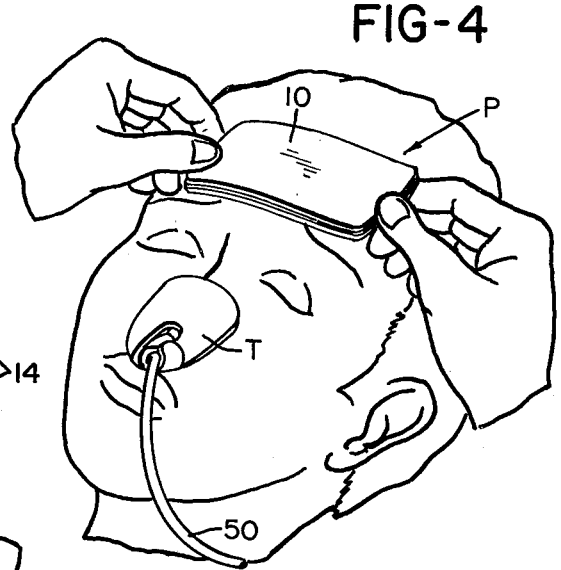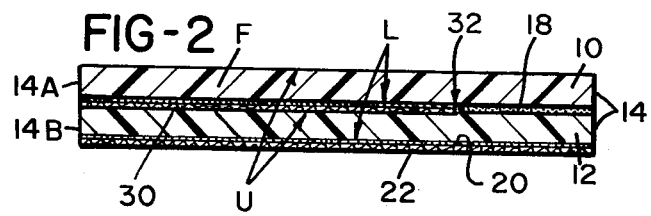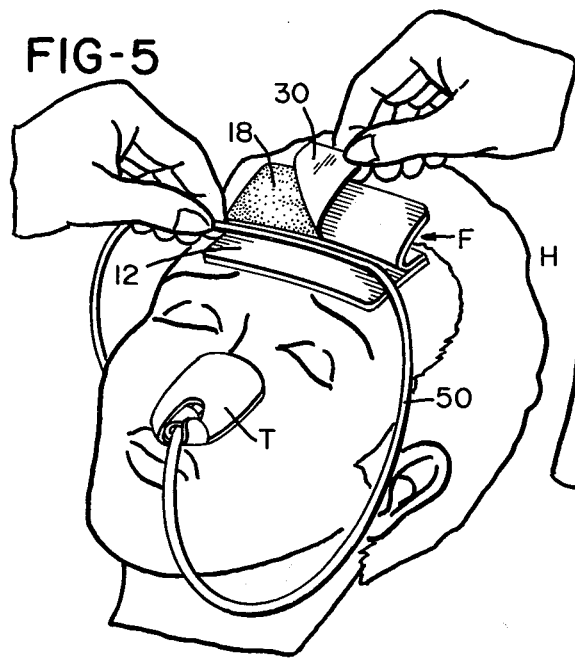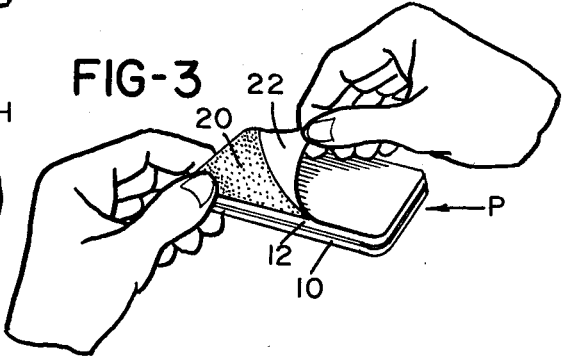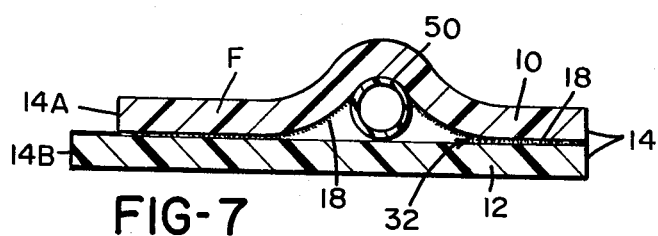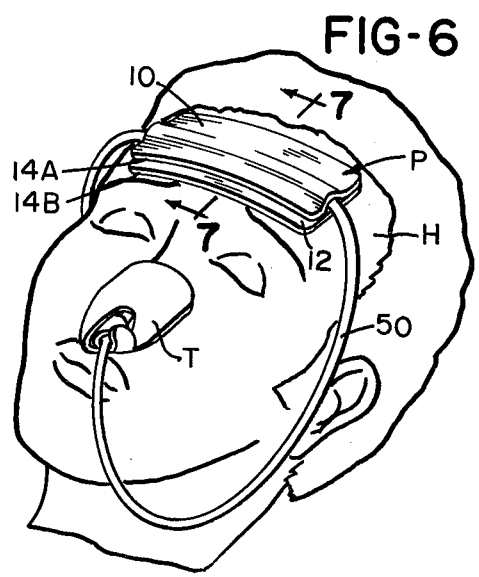

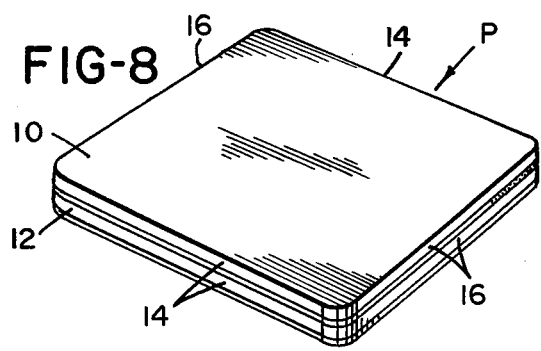
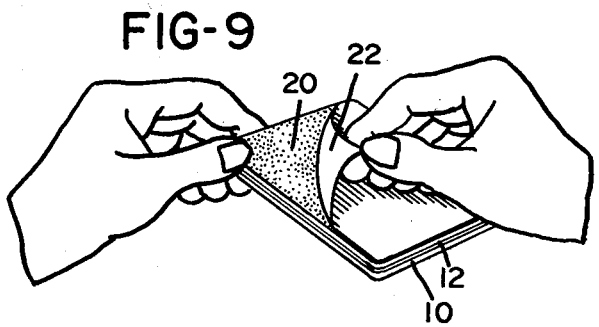
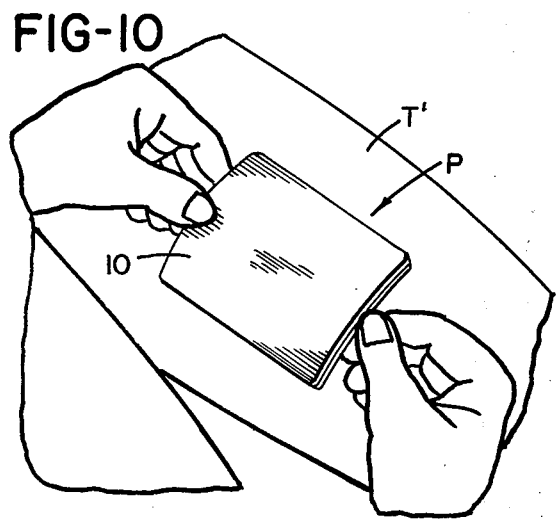
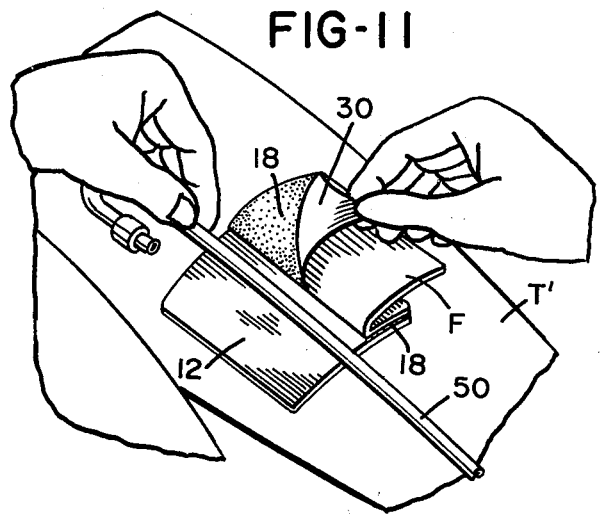
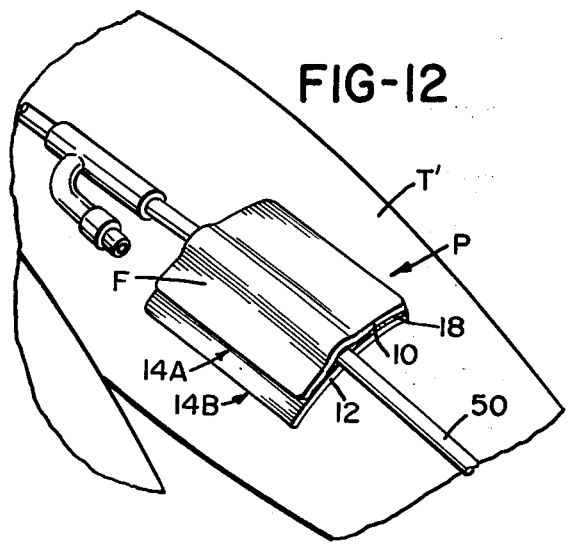

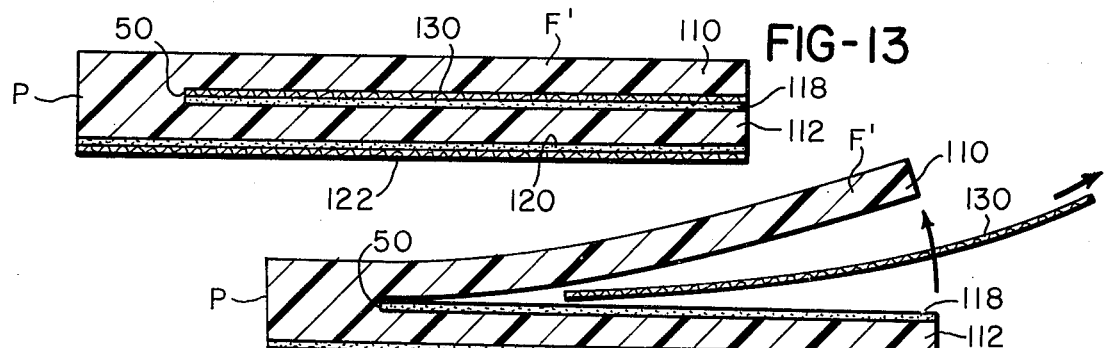
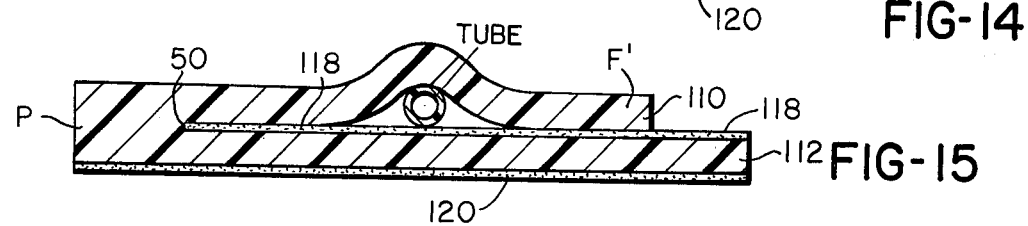
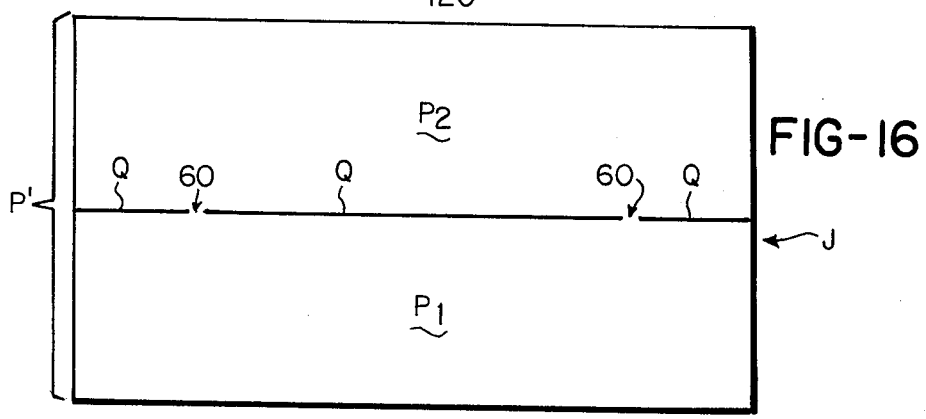
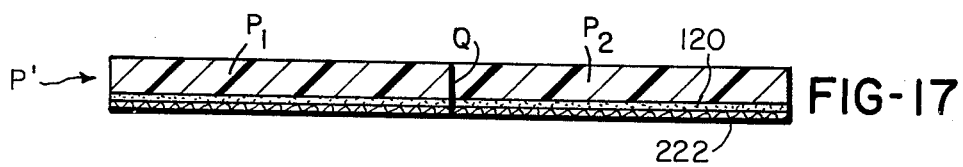
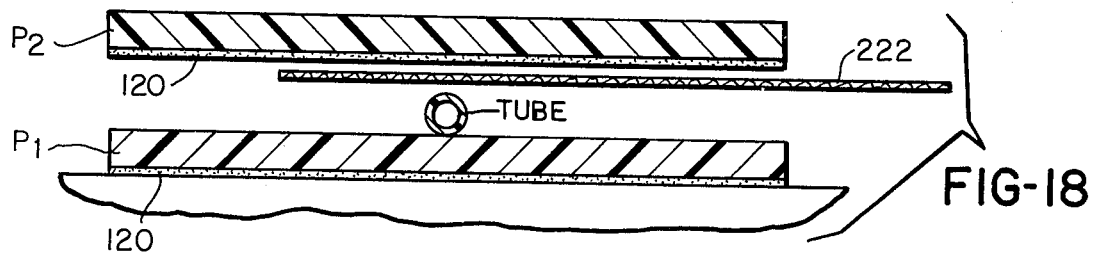
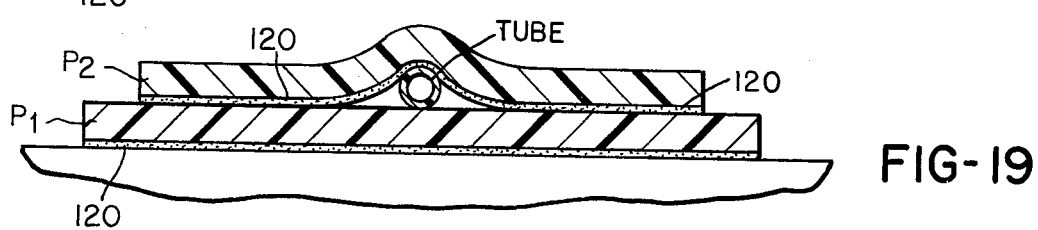

PAD FOR ANCHORING AN ARTICLE TO THE SKIN OF A PATIENT

BACKGROUND OF THE INVENTION

1. Field of the Invention

The invention relates to flexible securement devices for articles such as by way of example, catheter tubing and the like.

2. Description of the Prior Art

U.S. Pat. No. 3,430,300 to M. Doan discloses two embodiments of a fastener for medical tubes wherein the fasteners are fabricated from a unitary strip of adhesive material such as cloth. In one embodiment the strip of material is T-shaped whereby the top of the T is adapted to be folded down to engage the stem of the T for securing it in folded relationship with respect to a medical tube as illustrated in FIGS. 1-3 of said patent. The second embodiment utilizes an elongate strip, the end portion of which is adapted to be folded over a tube and thereafter threaded through a longitudinal slit 37 which is disposed centrally of the strip at a location below the tube for securing the upper portion of the strip to the tube as illustrated in FIGS. 4-7. In each of the embodiments one end portion of each strip is provided with an adhesive for securing the strip to a support at a location which is spaced from the location of the tube, whereby considerable relative movement is provided between the tube and the surface to which the fastener strip is secured.

U.S. Pat. No. 3,834,380 to S. A. Boyd discloses a holder for I.V. injection cannula and tubing in the form of an elongate longitudinally split clamping tube 20 which is either molded integrally with or adhesively secured transversely to the upper surface of a length of tape. The split clamping tube is adapted to receive a catheter tube or the like after which the clamping tube is closed onto the catheter tube by means of interlocking pads 23 and 24 of artificial burr material 23 and 24 or by means of strap fasteners. Pads 23 and 24 are secured to and carried by an adhesive strip the lower surface of which is adapted to be fastened to the body of a patient by means of adhesive on the lower surface of said strip.

U.S. Pat. No. 3,146,778 to H. A. Krawiec discloses a catheter support which comprises a catheter-holding element 1 and a separate supporting member 10 which latter member is adhesively secured to the skin of a patient. The catheter-holding element is releasably attached to the supporting material by means of a strap fastener for securing tubing in such a manner that considerable relative movement can occur between the tube and the skin of a patient.

U.S. Pat. No. 3,918,446 to P. M. Buttaravoli discloses a securement device for an I.V. catheter and its tubing which comprises a pair of top and bottom pads which are interconnected centrally of their lengths to provide a pair of hinged flaps in the upper pad which overlies the lower pad as illustrated in FIGS. 1-8. The lower pad is provided with elongate slits, notches, and openings for accommodating an infusion needle and medicant. One of the flaps is adapted to secure the coupling portion 50 of a needle whereas the other flap is adapted to anchor a length of tubing which is connected to the coupling portion of a needle to the lower panel. In FIGS. 9-12 a modification is disclosed wherein a single piece of material is provided with an elongate hinge 66 which subdivides the piece into upper and lower portions, said portions being integrally hinged at 60 along mating edges 68 and 70. The lower portion 78 is provided with a notch 81 and openings 82 at opposite ends of through slits 76, as in the lower pad of FIGS. 1-8. The upper portion is adapted to be folded over the lower portion for securing the coupling portion of an infusion needle and I.V. tubing 50, between the pads, by means of an adhesive.

Other prior art holders for securement devices known to applicant are embodied in U.S. Pat. No. 2,449,882 to A. J. Daniels; No. 3,138,158 to D. W. Gordon et al; No. 3,046,984 to F. O. Eby; No. 3,286,713 to L. D. Kurtz et al; No. 3,683,911 to J. B. McCormick; No. 3,724,456 to R. Waxman; No. 3,726,280 to A. L. Lacount; No. 3,630,195 to L. S. Santomieri; No. 3,613,663 to R. P. Johnson; No. 3,367,332 to J. N. Groves; No. 3,542,321 to R. D. Kahabka; No. 3,782,378 to S. J. Page; No. 2,814,294 to F. H. J. Figge; No. 2,159,947 to I. Gansel; No. 2,669,231 to B. Fisher; No. 3,677,250 to M. T. Thomas; and No. 3,670,727 to D. L. Reiterman.

SUMMARY OF THE INVENTION

The invention is directed to a flexible pad of soft, strong, foam material having a flap formed integrally therewith, whereby an article, such as a catheter tube or the like, placed beneath the flap, may be securely anchored to the pad, the lower surface of which includes adhesive means by which the pad is adapted to be fastened to the skin of a patient for securely affixing the article anchored by the pad relative to the body of a patient.

The pad is adapted to be packaged in a sterile environment for one time use. The adhesively coated surfaces of the pad are provided with removable release strips which protect and maintain the effectiveness of the adhesive for its intended use.

Once a pad has been adhesively secured to the skin of a patient the flap portion of the pad may, in certain forms of the invention in which the flap is hingedly secured relative to the pad, be easily lifted from a lowered to an elevated position for permitting the insertion of a catheter tube or the like onto that portion of the pad which the flap, before being raised, covered.

In other forms of the invention the flap portion is not hingedly connected to the pad in which event it is disposed in overlying relationship with the pad to which it is adhesively secured for anshoring an article between the pad and flap.

The subject pad is particularly adapted to secure nasal tubes to the forehead of a patient, and to anchor Foley catheters and catheter tubes to a patient's leg or abdomen. Heretofore Foley catheters were secured to the leg of a patient by means of straps which encircled the leg and it was not uncommon for such straps to impair the free flow of blood through the leg.

BRIEF DESCRIPTION OF THE DRAWINGS

FIG. 1 is a perspective view of a securement pad embodying the teachings of the present invention.

FIG. 2 is a sectional view of the pad of FIG. 1 taken on line 2—2 thereof.

FIG. 3 is a perspective view illustrating the manner in which the lower adhesive surface of the pad is exposed for application to a support surface such as the skin of a patient.

FIG. 4 is a perspective view illustrating the manner in which the pad of FIG. 3 is initially applied to the forehead of a patient.

FIG. 5 illustrates the manner in which adhesive on the under surface of the pad is exposed incident to the anchoring of a catheter tube to the patient.

FIG. 6 is a view similar to FIG. 5 showing the pad with the flap thereof in a lowered position for securing the catheter tube to the pad.

FIG. 7 is a sectional view taken on line 7—7 of FIG. 6.

FIG. 8 is a view similar to FIG. 1 illustrating the shape of the pad embodying the details of the present invention which has been designed for facilitating the attachment of a Foley catheter to the thigh of a patient.

FIGS. 9, 10, 11 and 12 diagrammatically illustrate the various steps which are followed in securing a Foley catheter tube to the thigh T of a patient using the pad of FIG. 8.

FIGS. 13–15 are sectional views of a modification of the pad of FIGS. 1 and 8.

FIG. 16 is a top plan view of another modification of the pad of the present invention.

FIG. 17 is an end view of the pad of FIG. 16.

FIGS. 18 and 19 are side views of the pad of FIG. 16, illustrating the manner in which the pad of FIG. 16 is used.

DESCRIPTION OF THE PREFERRED EMBODIMENTS

With particular reference now to FIGS. 1, 2, and 8, the letter P denotes generally a pad which embodies the teachings of the present invention and wherein the numerals 10 and 12 denote generally a pair of like-size panels formed of soft, flexible foam material each of which include side and end edges 14 and 16 respectively, and each of which include an upper surface U and lower surface L. In the preferred embodiment of the invention the lower surface L of each of panels 10 and 12 are provided with an adhesive denoted by the numerals 18 and 20 respectively. The adhesive on the lower surface of the lower panel 12 is covered by a removable release or backing sheet 22.

A second release or backing sheet 30 which is of a lesser width than sheet 22, is adhesively secured to the adhesive 18 on the lower surface of the upper panel 10 for defining a flap F which overlies a corresponding portion of the upper surface of the lower panel 12. As best illustrated in FIG. 2, the adhesive 18 beyond side end 32 of the second backing sheet 30 secures or bonds corresponding portions of the lower surface of the upper panel to portions of the upper surface of the lower panel.

The pad of FIGS. 1 and 8 is fabricated from soft, flexible, foam material which is odor free and non-irritating to the skin of the patient and the adhesive, and in particular adhesive 20 which is adapted to engage the skin of a patient for affixing the pad to a patient is hypoallergenic in nature, being formulated in such a manner as to be non-irritating to the skin of a patient over a period of several days.

The pads of FIGS. 1 and 8 are preferably individually packaged and sterilized whereby to be ready for use upon opening of the package.

In those instances in which it is necessary or desirable to anchor a catheter tube 50 to the forehead of a patient, such as by way of example, when a tube has been inserted into the nasal passage of a patient and there suitably secured by means of a securement device denoted generally by the letter T, the first backing sheet 22 is removed from the lower surface of the pad for thereby exposing adhesive 20, note FIG. 3, after which the pad is adapted to be secured to the forehead H of a patient as in FIG. 4 by means of adhesive 20. After the pad has thus been secured to the forehead of a patient flap F thereof is raised for permitting a length of catheter tubing 50 to be interposed between the aforesaid surfaces of the flap and the lower panel. The second backing sheet 30 may then be removed as illustrated in FIG. 5 after which flap F is lowered onto tube 50 and onto the other surface of the pad to which the flap is securely anchored as illustrated in FIGS. 6 and 7. Reference is made to U.S. Pat. No. 3,046,989 to E. J. Hill for details of the securement device T.

The pad of FIG. 8 is of a different shape from the pad of FIG. 1, but it may be fabricated in a manner similar to FIG. 1; however, the pad of FIG. 8 is substantially rectangular whereby to more readily adhere to a patient's leg or abdomen such as, by way of example, when securing a Foley urinary catheter or when securing a drain tube or the like to the thigh and/or abdomen of a patient.

It should be understood that if desired, adhesive 18 instead of being applied to the under surface of the upper panel 10 can be applied to the upper surface of the lower panel 12, in which event the removable backing sheet 30 would overlie the said adhesive on the lower panel and thereby define the unattached area of the flap F.

As illustrated in FIGS. 13–15, the pad P may be fabricated from a single piece of soft, strong, resilient material the thickness of which is equal the combined thickness of the upper and lower panels 110 and 112 and wherein the flap F' is formed by cutting, slitting, or otherwise bisecting the thickness of the pad for providing a flap F' hingedly secured at 50 along a side edge to and integral with the pad per se. The lower surface of the pad is provided with adhesive 118 covered by a first backing sheet 122.

The upper surface of the pad is provided with adhesive 118 which is covered by a second backing sheet 130, or alternatively, the under surface of the flap F' may be provided with adhesive which is covered by a second backing sheet.

When flap F' is raised, as in FIG. 14, the backing sheet 130 may be removed from the adhesive surface which it covers and an article, such as a catheter tube T inserted beneath the flap which when lowered, as in FIG. 15, will firmly anchor the article, as illustrated.

As best illustrated in FIGS. 6, 7, and 12 the free side edge 14A of flap F does not extend out as far as free side edge 14B of the lower pad 12 when an article has been anchored by reason of the presence of an article such as tube 50 beneath the flap.

A pad wherein adhesive 18 is on the upper surface of that portion of the pad which is disposed beneath flap F, enables an article, such as a catheter tube to be more easily anchored to the pad than when the adhesive is on the lower surface of the flap, by reason of the fact that the lower surface of the pad is already secured to the skin of a patient before the flap is lifted to receive an article, and when the upper surface of the pad which is exposed incident to raising the flap is adhesively coated, the article will have been secured to the pad before the flap is lowered, thereby lessening the tendency for relative motion to occur between a catheter tube and the skin of a patient to which the pad has been secured.

With particular reference to FIGS. 8–12, it will be noted that pad P is substantially rectangular for providing a greatly increased "anchor" area than the "anchor" area of the pad of FIGS. 1-6. The pad of FIGS. 8-12 is particularly well adapted to secure a Foley catheter relative to the thigh T' of a patient, or for securing, by way of example, a catheter tube to the abdomen or back of a patient by means of strap-like members which encircled the thigh and it was not uncommon for such members to interfere with the normal flow of blood through an encircled limb.

The pad P of FIGS. 9-12, like the pad of FIGS. 1-8, being of a soft, but strong, material minimizes discomfort by allowing a patient's skin to breath, and it allows a Foley catheter tube to bend without kinking or collapsing.

In the pad of FIGS. 1-6 the width of the flap F as measured inwardly from its free side edge 14A is about 50% of the overall side-to-side width of the pad, whereas in the pad of FIGS. 9-12 the width of the flap is about 80 to 85% of the overall side-to-side width of the pad.

In FIGS. 16-19 I have illustrated a second modification of my invention, which differs from the disclosure of FIGS. 1-15 in that a retainer flap is not hingedly secured to a mounting pad, such as 12, but is initially attached via a line of weakening as defined by through slits Q the ends of which are spaced apart as at 60 for providing small, frangible, easily ruptured, connector tabs.

The letter P' denotes a pad of soft, strong, flexible material the lower surface of which is provided with an adhesive 120 which is suitably covered by removable backing strip 222. Pad P' is subdivided, via the aforesaid line of weakening, into a pair of panels $P_1$ and $P_2$ which may be of the same or different areas. Pads P' are suitably housed within a sterile envelope and delivered to the ultimate user in the flat form illustrated in FIGS. 16 and 17.

When pad P' is to be used it is subdivided into the panels $P_1$ and $P_2$ after which panel $P_1$ may be adhesively affixed to the skin of a patient upon removal of the removable backing strip 222 of panel $P_1$.

Then, as illustrated in FIG. 18 the removable backing strip 222 of panel $P_2$ is removed for exposing adhesive surface 120 of said panel. An article, such as a catheter tube 50 may be interposed between panels $P_1$ and $P_2$, and when panel $P_2$ is lowered, as in FIG. 19, into contact with portions of the upper surface of panel $P_1$ the article will be firmly anchored therebetween.

If desired the pad P' may, by way of example, be completely severed as by means of a slit or through cut Q, wherein the removable backing strip would be provided with alternate slits Q and tabs 60 of such a nature as to maintain panels $P_1$ and $P_2$ in coplanar relationship as in FIG. 16, against their accidental or unintentional separation. Or, the backing strip may be completely severed by means of a slit or through cut Q in which event the pad P' would be provided with alternate slits Q and connector tab 60. In other instances only the pad may be provided with slits Q and connector tabs 60 and wherein the removable backing strip is intact, free of lines of weakening, in which event panel $P_1$ would first be stripped from the backing strip and secured to the skin of a patient, after which panel $P_2$ would be stripped and applied as in FIG. 19.

To summarize, suitable means in the form of lines of weakening in both pad P' and removable backing strip 222, or in one or the other of pad P' and weakening strips 222 may be provided for defining and releasably interconnecting panels $P_1$ and $P_2$, in coplanar relationship.

Uniformly satisfactory results have been obtained in those instances in which the pad material is fabricated from foamed polyvinyl chloride, and wherein the adhesive is Rohm & Haas No. N580 Acrylic water emulsion adhesive.

What is claimed is:

1. A composite pad of flexible material securable to the skin of a patient for anchoring an article, such as a catheter tube or the like thereto, comprising an upper panel and a lower panel each having side and end edges, and upper and lower surfaces with the upper surface of the lower panel confronting the lower surface of the upper panel; an adhesive coating the lower surface of the lower panel; a first removable backing sheet overlying the adhesive surface of the lower panel; an adhesive coating interposed between said upper and lower panels; a portion of the lower surface of the upper panel in contacting, adhesively secured, overlying relationship with a like portion of the lower panel; a second removable backing sheet in face-to-face relationship with the confronting surfaces of said upper and lower panels and overlying and coating, the interposed adhesive coating said upper panel including a flap which is integral with, and hingedly secured, along an edge to that portion of the upper panel which is secured to the lower panel; the lower surface of the lower panel adapted to be affixed to the skin of a patient upon removal of the first backing sheet; the lower surface of the flap adapted to be affixed to the underlying portion of the upper surface of the upper panel upon removal of the second backing sheet for anchoring an article, interposed between the adjacent surfaces of the flap and the lower panel to the pad.

2. A pad as called for in claim 1, wherein the second mentioned adhesive is on the lower surface of the upper panel.

3. A pad as called for in claim 1, wherein the second mentioned adhesive is on the upper surface of the lower panel.

4. A pad as called for in claim 1, wherein each of said panels are of the same size and characterized by an absence of slits, notches, or openings therein.

5. A pad as called for in claim 1, wherein that portion of the upper panel which is initially adhesively secured to a lower panel extends inwardly from a common side edge and between corresponding opposite end edges of said panels.

6. A pad as called for in claim 1, wherein the flap extends between the end edges and inwardly from a side edge of the upper panel and wherein the width of said flap measured inwardly from its side edge is from 50% to 80% of the overall side-to-side width of the pad.

7. A pad as called for in claim 1, wherein the pad is substantially rectangular in shape.

8. A pad of soft flexible material securable to the skin of a patient for anchoring an article such as a catheter tube or the like thereto, comprising:

a substantially rectangular body having upper and lower outer surfaces defining a thickness configuration for said body, a pair of side edges, and a pair of end edges, said thickness being divided throughout a major portion of the width of the body to define a pair of identical coextensive upper and lower flaps which both extend between the end edges and inwardly from one side edge of said body toward the other side edge of the body, said upper and lower flaps each having upper and lower surfaces with the upper surface of said lower flap confronting the lower surface of the upper flap, and wherein the inner ends of said flaps are interconnected throughout their entire length at a location inwardly from the other side edge of said body;

adhesive means to affix the entire lower surface of the pad between all of said edges including the lower surface of the lower flap located along said body other side edge to the skin of a patient;

an adhesive coating interposed between said upper and lower flaps to affix the lower surface of the upper flap to an underlying portion of the upper surface of the lower flap for anchoring an article positioned between said upper and lower flaps to the lower flap of the pad; and a removable backing sheet in face-to-face relationship with the confronting surfaces of said upper and lower flaps and overlying and contacting the interposed adhesive coating.

9. A pad as called for in claim 8, wherein the width of the flaps measured inwardly from their free side edges approximates 80% of the overall side-to-side width of the pad.

10. A pad as called for in claim 8, further including a removable backing sheet covering said adhesive means.

11. A pad as called for in claim 8, wherein the adhesive coating is positioned on the upper surface of that portion of the lower flap which underlies the upper flap.

12. A pad as called for in claim 11, wherein the adhesive coating is on the lower surface of the upper flap.

13. A pad as called for in claim 8, wherein the width of the flaps measured inwardly from their free side edges approximates 50% of the overall side-to-side width of the pad.

14. A pad as called for in claim 8, wherein said adhesive coating includes pressure-sensitive adhesive.

* * * * *